(12) United States Patent
Nishiya et al.

(10) Patent No.: US 6,844,426 B2
(45) Date of Patent: Jan. 18, 2005

(54) MAGNETIC CARRIER CAPABLE OF BINDING WITH PROTEIN AND PURIFICATION METHOD OF PROTEIN UTILIZING THE MAGNETIC CARRIER

(75) Inventors: Yoshiaki Nishiya, Tsuruga (JP); Mikio Kishimoto, Moriya (JP)

(73) Assignees: Toyo Boseki Kabushiki Kaisha, Osaka (JP); Hitachi Maxell, Ltd., Osaka (JP)

( * ) Notice: Subject to any disclaimer, the term of this patent is extended or adjusted under 35 U.S.C. 154(b) by 0 days.

(21) Appl. No.: 10/359,303

(22) Filed: Feb. 6, 2003

(65) Prior Publication Data

US 2003/0166878 A1 Sep. 4, 2003

(30) Foreign Application Priority Data

Feb. 6, 2002 (JP) ........................................ 2002-029751

(51) Int. Cl.[7] .............................................. C07K 17/00
(52) U.S. Cl. .................... 530/412; 252/62.56
(58) Field of Search ........................ 530/412; 252/62.56

(56) References Cited

U.S. PATENT DOCUMENTS

| 4,452,773 | A | * | 6/1984 | Molday | 424/1.37 |
|---|---|---|---|---|---|
| 4,687,748 | A | * | 8/1987 | Schroder | 436/526 |
| 4,965,007 | A | * | 10/1990 | Yudelson | 252/62.53 |
| 5,310,663 | A | | 5/1994 | Dobeli et al. | |
| 6,312,910 | B1 | | 11/2001 | Vellinger et al. | |
| 2001/0034017 | A1 | | 10/2001 | Rauth et al. | |

FOREIGN PATENT DOCUMENTS

| EP | 0 286 239 A1 | 10/1988 |
|---|---|---|
| EP | 0 656 368 A | 6/1995 |
| EP | 1 069 131 A1 | 7/2000 |

OTHER PUBLICATIONS

J.C. Smith et al., "Chemical Synthesis and Cloning of a Poly(arginine)–coding Gene Fragment Designed to Aid Polypeptide Purification," Gene, vol. 32, pp. 321–327, Elsevier, 1984.

J. Germino et al., "Use of Gene Fusions and Protein–Protein Interaction in the Isolation of a Biologically Active Regulatory Protein: The Replication Initiator Protein of Plasmid R6K," Proc. Natl. Acad. Sci., vol. 80, pp. 6848–6852, Nov. 1983.

B. Nilsson et al., "Efficient Secretion and Purification of Human Insulin–like Growth Factor 1 with Gene Fusion Vector in staphylococci," Nucleaic Acids Research, vol. 13, No. 4, 1151–1163, 1985.

Keiichi Itakura et al., "Expression in *Escherichia Coli* of a Chemically Synthesized Gene for the Hormone Somatostatin," Science, vol. 198, pp. 1056–1063, 1997.

Plaga S et al.: "SP–A Binding Sites on Bovine Alveolar Macrophages" Experimental Cell Research, vol. 245 no. 1, Nov. 25, 1998, pp. 116–122, XP002269241 *p. 117*.

* cited by examiner

*Primary Examiner*—Karen Cochrane Carlson
*Assistant Examiner*—Anand U Desai
(74) *Attorney, Agent, or Firm*—Morrison & Foerster LLP

(57) ABSTRACT

The present invention provides a strikingly convenient novel purification method of protein, as compared to conventional methods, which affords automation and high throughput, and a material therefor. That is, the present invention provides a magnetic carrier containing a ferromagnetic oxide particle and a carbohydrate layer coating the ferromagnetic oxide particle, a purification method of protein using the carrier, and a reagent kit for purification of protein.

20 Claims, 3 Drawing Sheets

1~6: samples before purification (cell lysate)
M: molecular weight marker

7~12: purified proteins
M: molecular weight marker

1: amylose-coated magnetite particle immediately after dispersion in aqueous solution
2: amylose-coated magnetite particle 30 days refrigerated (4°C) after dispersion in aqueous solution 1,2: amylose-coated magnetite particle of the invention
3,4: commercially available amylose-coated resin
M: molecular weight marker 1: eluted with phosphate buffer
2: eluted with Tris buffer
M: molecular weight marker

MAGNETIC CARRIER CAPABLE OF BINDING WITH PROTEIN AND PURIFICATION METHOD OF PROTEIN UTILIZING THE MAGNETIC CARRIER

TECHNICAL FIELD OF THE INVENTION

The present invention relates to a magnetic carrier preferably used for purifying a protein from a biological sample containing the objective protein, a production method thereof, a purification method of protein utilizing the magnetic carrier, and a reagent kit for purification of protein.

BACKGROUND OF THE INVENTION

Various kinds of methods, substances and approaches have been conventionally known for extraction or purification of a particular objective protein from other components in a sample, such as bacteria, yeast, insect cells, animal cells, animal tissues, plant tissues (including lysate, extract and the like obtained from these), cell-free protein synthesis solutions and the like (hereinafter these are generally referred to as a "biological sample").

One example of general approach utilizes nonspecific affinity of a protein for a carrier. As such approach, for example, ion exchange chromatography based on the electric charge of protein molecule is known. In ion exchange chromatography, a protein mixture is added to a chromatography matrix having an opposite electric charge from the protein, and various proteins are allowed to bind with the matrix by reversible electrostatic interaction. The protein bound with the matrix can be eluted in the order of from one having a weaker bond to one having a stronger bond, by increasing the ionic strength or changing the pH of the elution buffer.

An example of other general approach is one utilizing the physical property of the protein as a means for separation. This approach is represented by known gel filtration based on the size of protein. In gel filtration, a protein mixture is applied to a gel filtration column packed with a matrix for chromatography having a given size of pores. Thereafter, elution is done using an eluent (generally buffer) to obtain individual chromatography fractions, which are subjected to analysis.

A still another example of the general approach is one utilizing specific affinity of protein for a reagent for purification. Known examples of such approach include affinity chromatography utilizing an antibody capable of specific adsorption to the objective protein, and, when the objective protein is an antibody, an antigen capable of specific adsorption to said antibody. In the affinity chromatography, generally, antibody or antigen is bound with a column substrate, and a solution containing an antigen or antibody capable of specifically adsorbing to said antibody or antigen is applied to the column, thereby to form an immune complex (antigen-antibody complex) on the column substrate. Subsequently, for example, the above-mentioned immune complex is exposed to a buffer having an extremely high ionic strength or a buffer having an extremely high or low pH buffer to instabilize the immune complex into elution. Thus, affinity chromatography is a highly effective purification method of protein based on the specific interaction between the objective protein and ligand immobilized on the solid phase. In affinity chromatography, generally, a solid phase ligand has several inherent scientific properties and due to such properties, it affords selective adsorption of the objective protein. Contaminant proteins can be removed because they do not bind with a solid phase ligand or by washing the solid phase ligand with a suitable solution.

The possibility of preparation of hybrid gene by recent gene technology has opened a new avenue. That is, by binding a gene sequence encoding a desired protein with a gene sequence encoding a protein fragment (affinity peptide) having high affinity for the ligand, a recombinant protein having an affinity peptide suitable for the above-mentioned separation can be expressed, which in turn has made it possible to purify a desired recombinant protein in the form of a fusion protein by a single step of purification using the affinity peptide. In addition, by mutation restricted to a certain site, a specific chemical or enzymatic cleavage site can be introduced into the binding site of the affinity peptide and the desired recombinant protein, in which case the fusion protein is purified using a suitable affinity resin and the affinity peptide is cleaved chemically or enzymatically to recover the desired recombinant protein. Such purification method is known from, for example, Science 198, 1056–1063 (1977) (by Itakura et. al), Proc. Natl. Acad. Sci. U.S.A. 80, 6848–6852 (1983) (by Germino et al.), Nucleic Acids Res. 13, 1151–1162 (1985)(by Nilsson et. al.), Gene 32, 321–327 (1984) (by Smith et al), U.S. Pat. No. 5,284,933 and U.S. Pat. No. 5,643,758.

The affinity peptide of fusion protein can be directly or indirectly bound with a biochemically active polypeptide or protein. When a single affinity peptide is used, the affinity peptide can be bound with the amino terminal amino acid or carboxyl terminal amino acid of a biochemically active polypeptide or protein. When two affinity peptides are used, one of the affinity peptides may be bound with the amino terminal amino acid of a biochemically active polypeptide or protein and the other affinity peptide may be bound with the carboxyl terminal amino acid of the biochemically active polypeptide or protein.

In the case of an indirect binding, the affinity peptide contains a suitable selective cleavage site and can be bound with a desired biochemically active polypeptide or protein via said selective cleavage site. Known preferable selective cleavage sites are amino acid sequences -(Asp)$_n$-Lys- wherein n is 2, 3 or 4 and -Ile-Glu-Gly-Arg-. These selective cleavage sites can be specifically recognized by enterokinase and aggregating factor Xa, respectively, which are proteases. Such affinity peptide can be enzymatically cleaved at the above-mentioned selective cleavage sites by a method known per se.

In the case of direct binding, the affinity peptide remains bound with a desired biochemically active polypeptide or protein. That is, the affinity peptide does not have a chemically or enzymatically cleavable selective cleavage site. The direct bond is advantageous when the activity of the desired polypeptide or protein is not adversely affected by the presence of affinity peptide.

U.S. Pat. No. 5,643,758 discloses a binding protein having an affinity peptide having specific affinity for particular carbohydrate; in other words, a production method of a fusion protein using a carbohydrate-binding protein and a convenient purification method using it. The above-mentioned carbohydrate-binding protein is exemplified by mono, di or polysaccharide-binding protein, which is more specifically a maltose-binding protein, an arabinose-binding protein or the like. Particularly, the maltose-binding protein, which is a malE gene product of *Escherichia coli*, is a periplasm protein subject to an influence of osmotic pressure, and shows specific affinity for maltose and maltodextrin. This maltose-binding protein, its fragment, and a fusion protein with an objective protein can be purified by affinity column chromatography using an amylose resin. Those of ordinary skill in the art know that utilization of a maltose-binding protein as an affinity peptide of fusion protein leads to a high possibility of purification in a solubilized state, even when the objective protein is sparingly soluble or easily insolubilized.

As mentioned above, there are various purification methods of protein, among which affinity column chromatography utilizing fusion protein is particularly a highly superior purification method. These methods generally include regeneration and recycled use of expensive materials used, such as carrier and the like, which renders it not entirely convenient. The conventional purification method mainly based on column chromatography requires a lot of time for sequentially passing samples through column, due to which automation and high throughput are difficult to achieve.

The present invention has been made to solve the above-mentioned problems and provides a purification method of protein, which is strikingly convenient as compared to conventional methods and which permits automation and high throughput, and materials therefor.

SUMMARY OF THE INVENTION

As a result of intensive studies made by the present inventors in an attempt to develop a convenient purification method of protein, which permits automation and high throughput, they have taken note of specifically easy binding of amylose with a maltose-binding protein, bound the maltose-binding protein with a ferromagnetic oxide particle surface-treated with amylose as a representative carbohydrate, and tried purification of this protein from a biological sample, which resulted in efficient isolation of the protein.

Accordingly, the present invention provides the following.

(1) A magnetic carrier comprising a ferromagnetic oxide particle and a carbohydrate layer coating the ferromagnetic oxide particle.
(2) The magnetic carrier described in the above-mentioned (1), wherein the ferromagnetic oxide is ferromagnetic iron oxide.
(3) The magnetic carrier described in the above-mentioned (2), wherein the ferromagnetic iron oxide is at least one member selected from maghemite, magnetite and manganese zinc ferrite.
(4) The magnetic carrier described in any of the above-mentioned (1) to (3), wherein the carbohydrate forming the carbohydrate layer is oligosaccharide or polysaccharide comprising glucose as a main unit.
(5) The magnetic carrier described in the above-mentioned (4), wherein the carbohydrate forming the carbohydrate layer is amylose.
(6) The magnetic carrier described in any of the above-mentioned (1) to (5), which has saturation magnetization of 20 A·m$^2$/kg–100 A·m$^2$/kg.
(7) The magnetic carrier described in any of the above-mentioned (1) to (6), showing a coercive force of not more than 15.93 kA/m.
(8) The magnetic carrier described in any of the above-mentioned (1) to (7), having an average particle size of 0.05 μm–20 μm.
(9) The magnetic carrier described in any of the above-mentioned (1) to (8), which maintains, after preservation in a dispersion solution at 2–10° C. for 30 days, not less than 80% of the protein binding capability before the preservation.
(10) The magnetic carrier described in any of the above-mentioned (1) to (9), which has relatively high affinity for a fusion protein containing a part or the entirety of a protein capable of specifically binding with carbohydrate and having affinity for carbohydrate, rather than the protein itself.
(11) The magnetic carrier described in the above-mentioned (10), which substantially binds 100% with a fusion protein containing a part or the entirety of a protein capable of specifically binding with carbohydrate and having affinity for carbohydrate, when a lysate of a recombinant that expresses the protein and the fusion protein is purified.
(12) The magnetic carrier described in any of the above-mentioned (1) to (11), which affords more efficient elution by the use of a phosphate buffer as an eluent for elution of a protein bound with the carrier, than by the use of a different buffer.
(13) The magnetic carrier described in the above-mentioned (12), wherein the protein bound with the carrier shows a recovery percentage of not less than 60% by a phosphate buffer and not more than 20% by a different buffer.
(14) A production method of a magnetic carrier, which is described in any of the above-mentioned (1) to (13), which comprises adding a carbohydrate to a dispersion of the ferromagnetic oxide particles, heating the mixture and cooling the mixture to form a carbohydrate layer coating the ferromagnetic oxide particles.
(15) A method for purifying a protein capable of specifically binding with carbohydrate from a biological sample containing the protein, which comprises the steps of
  (a) binding said protein with the magnetic carrier described in any of the above-mentioned (1) to (13),
  (b) isolating said protein bound with the magnetic carrier from the biological sample, and
  (c) separating said protein isolated from the biological sample from the magnetic carrier.
(16) A method for purifying a fusion protein containing a part or the entirety of a protein capable of specifically binding with carbohydrate and having affinity for carbohydrate from a biological sample containing the protein and the fusion protein, which comprises the steps of
  (a) binding said fusion protein with the magnetic carrier described in any of the above-mentioned (1) to (13),
  (b) isolating said fusion protein bound with the magnetic carrier from the biological sample, and
  (c) separating said fusion protein isolated from the biological sample, from the magnetic carrier.
(17) A reagent kit for purification of a protein, which comprises a magnetic carrier described in any of the above-mentioned (1) to (13), a dispersion medium for preparing a solution for protein extraction by dispersing the magnetic carrier, and an eluent capable of eluting the protein.
(18) A reagent kit for purification of a protein, which comprises a solution for protein extraction containing the magnetic carrier described in any of the above-mentioned (1) to (13) and an eluent capable of eluting the protein.

DETAILED DESCRIPTION OF THE INVENTION

Figure 1A:
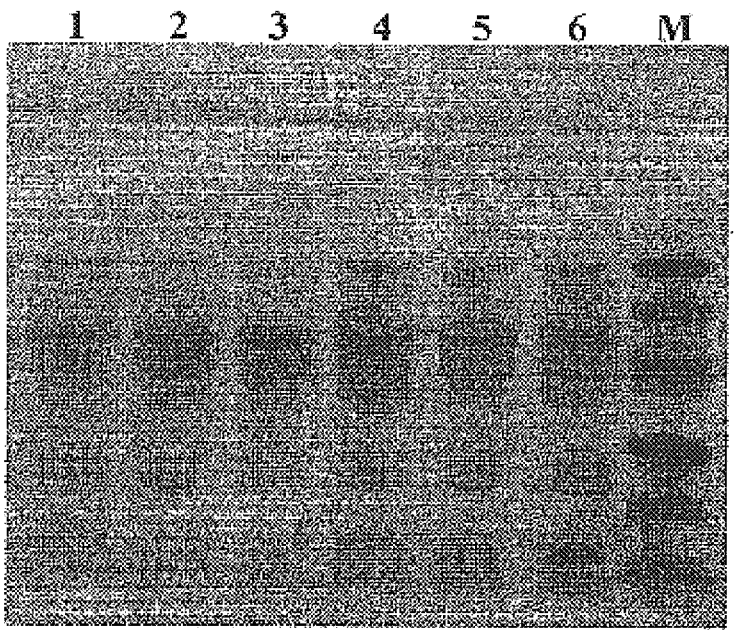
FIG. 1(a) shows comparison results of sodium dodecyl sulfate-polyacrylamide gel electrophoresis (hereinafter to be referred to as "SDS-PAGE") of the sample before purification.

The magnetic carrier of the present invention basically comprises a ferromagnetic oxide particle and a carbohydrate layer coating the ferromagnetic oxide particle, and is capable of binding with a protein.

The ferromagnetic oxide particle in the present invention is a particle obtained by oxidizing metallic particle and has magnetic reactivity (sensitivity to magnetic field). As used herein, by "has magnetic reactivity" is meant showing sensitivity to a magnetic field when an external magnetic field is present due to magnet and the like, such as magnetization by the magnetic field, adsorption to the magnet and the like. The ferromagnetic oxide is not particularly limited and exemplified by known metal oxides such as iron oxide, cobalt oxide, nickel oxide and the like. In view of superior sensitivity, particularly to a magnetic field, it is preferably ferromagnetic iron oxide. While ferromagnetic iron oxide is particularly preferable, any having superparamagnetism can be used as long as it is sensitive to a magnetic field. Examples of the ferromagnetic iron oxide include conventionally known various ferromagnetic iron oxides. Of these, at least one member selected from ferrites, such as maghemite ($\gamma$-$Fe_2O_3$), magnetite ($Fe_3O_4$), manganese zinc ferrite ($Mn_{1-x}ZnXFe_2O_4$) and the like is preferable, in view of superior chemical stability. Of these, magnetite, is particularly preferable because it shows high magnetization and is superior in sensitivity to the magnetic field.

The ferromagnetic iron oxide particle can be prepared by, for example, a conventionally known method comprising oxidization of particles, such as $Fe(OH)_2$ and the like, in water. In the Examples to be mentioned later, one example is directed to the manufacture of magnetite particles.

The ferromagnetic oxide particle to be used in the present invention is not particularly limited as regards the shape thereof and may be spherical, ellipsoidal, granular, plate, needle, polyhedral (e.g., cubic etc.), and the like. Preferred are spherical, ellipsoidal or granular one in view of easy processing into a preferable shape when prepared into the magnetic carrier to be mentioned below.

The size of the ferromagnetic oxide particle to be used in the present invention is also free of any particular limitation, but generally, one magnetic carrier is formed by coating a bulk of 1–100 particles with a carbohydrate layer, wherein the particle preferably has an average particle size of 0.05 $\mu$m–0.5 $\mu$m, because it facilitates formation of magnetic carrier having preferable size of 0.05 $\mu$m–20 $\mu$m, as mentioned below. The "particle size" of the ferromagnetic oxide particle refers to the maximum length of all the lengths in any direction of the particle. The average particle size of the above-mentioned ferromagnetic oxide particle is calculated by, for example, measuring the particle size of each of 300 particles on a transmission electron microscopic photograph and calculating the number average thereof.

The carbohydrate that forms a carbohydrate layer in the present invention is not particularly limited, and mono, di, or polysaccharide and mixtures thereof and the like can be used. A carbohydrate that has sufficient affinity for the objective protein may be selected and used as appropriate. Examples of such carbohydrate include glucose, galactose, arabinose, mannose, maltose, maltodextrin, amylose, dextrin, soluble starch and the like. Of these, oiligosaccharide or polysaccharide containing glucose as a main unit is preferable, and amylose is more preferable, because it is economical and easily available. Particularly when a fusion protein containing a part or the entirety of a maltose-binding protein is used as the objective protein, amylose is preferably used as a carbohydrate.

The magnetic carrier of the present invention comprises the aforementioned ferromagnetic oxide particle and a carbohydrate layer coating the particle. As used herein, by the "coating" is meant a carbohydrate layer formed as the outermost layer of the magnetic carrier by covering the outer periphery of the ferromagnetic oxide particle. The carbohydrate layer may be formed to completely cover the ferromagnetic oxide particle or the ferromagnetic oxide particle may be partially exposed as long as the affinity bond between the objective protein and the carbohydrate is not inhibited.

The carbohydrate layer need only be formed on the outermost part of the magnetic carrier, and as long as the magnetic reactivity of the magnetic carrier imparted by the ferromagnetic oxide particle is not impaired, an intermediate layer may be formed between the ferromagnetic oxide particle and the carbohydrate layer. Specifically, a magnetic silica bead wherein a ferromagnetic oxide particle is covered with a silica coating, and a magnetic carrier wherein a carbohydrate layer is formed on a particle that underwent processing such as dispersing ferromagnetic oxide particle in silica and the like (in this case, an intermediate layer is formed by silica) are exemplified. The presence of an intermediate layer made of silica between the ferromagnetic oxide particle and the carbohydrate layer affords a magnetic carrier advantageous in that it can form a near spherical particles. When an intermediate layer is formed using silica, a carbohydrate layer is preferably formed to completely cover the intermediate layer, thereby to avoid contamination of the nucleic acid.

In the magnetic carrier of the present invention, the amount of the carbohydrate coating the ferromagnetic oxide particle (adhered amount of the carbohydrate layer) is preferably 1 wt %–30 wt %, more preferably 5 wt %–20 wt %, of the ferromagnetic oxide particle. When the amount of the above-mentioned carbohydrate is less than 1 wt % of the ferromagnetic oxide particle, the magnetic carrier tends to show lower binding performance with a protein, and when the amount of the above-mentioned carbohydrate exceeds 30 wt % of the ferromagnetic oxide particle, it exerts an adverse influence on the magnetic properties of the magnetic carrier, which in turn often degrades the efficiency of the extraction and purification of the protein utilizing the magnetic field to be mentioned below.

The magnetic carrier of the present invention may be formed as one magnetic carrier by coating one ferromagnetic oxide particle with a carbohydrate layer, or plural ferromagnetic oxide particles may be coated with a carbohydrate layer to give one magnetic carrier. Generally, 1 to 100 ferromagnetic oxide particles are coated with a carbohydrate layer and provided as one magnetic carrier.

The magnetic carrier of the present invention is subject to no particularly limitation as to its shape, and may have various shapes, such as needle, sphere, plate and the like. However, spherical, ellipsoidal or granular carrier is preferable, because collection efficiency and dispersibility of the magnetic carrier are well-balanced during recovery of the magnetic carrier using a magnetic field and separation of the protein bound with the magnetic carrier from a biological sample, thus affording superior operability. As used herein, by the "spherical" is meant a shape having an aspect ratio (ratio of maximum length and minimum length as measured in any direction) of 1.0–1.2 (not less than 1.0 and not more than 1.2), and by the "ellipsoidal" is meant a shape wherein the aspect ratio exceeds 1.2 and is not more than 1.5. By the "granular" is meant one having the same length of particle in all directions, such as a sphere, and one free of particular anisotropy as a whole, though subject to change in length depending on the direction, such as an ellipsoid having a greater length in only one direction.

The size of the magnetic carrier is also free of any particular limitation, but one having an average particle size of 0.05 µm–20 µm is preferable, and 0.1 µm–10 µm is more preferable, because they show superior operability as do the above-mentioned shapes. When the average particle size of the magnetic carrier is less than 0.05 µm, the specific surface area of the magnetic carrier becomes large, often making the amount of binding with the objective protein greater but making collection of the magnetic carrier difficult. When the average particle size of the magnetic carrier exceeds 20 µm, the specific surface area of the magnetic carrier becomes smaller and the carrier tends to fall easily, thus often decreasing the amount of binding with the objective protein.

The "particle size" of the magnetic carrier means the same as the particle size of the aforementioned ferromagnetic oxide particle, and the average particle size of the magnetic carrier can be calculated in the same manner as in the average particle size of the aforementioned ferromagnetic oxide particle.

When a protein is purified using the magnetic carrier of the present invention utilizing a magnetic field, the magnetic properties of the magnetic carrier are important. The magnetic properties may be, for example, saturation magnetization mainly involved in the collection of the magnetic carrier bound with the protein, or coercive force mainly involved in the separation (elution of protein) of protein from the magnetic carrier.

In general terms, the higher the saturation magnetization is, the greater the sensitivity to the magnetic field becomes. Thus, a magnetic carrier showing high saturation magnetization improves collection performance of the magnetic carrier bound with a protein for the purification of a protein utilizing the magnetic field, but too high a saturation magnetization causes magnetic coherence.

The magnetic carrier of the present invention preferably shows saturation magnetization of 20 $A \cdot m^2/kg$ (emu/g)–100 $A \cdot m^2/kg$ (emu/g), more preferably 30 $A \cdot m^2/kg$ (emu/g)–80 $A \cdot m^2/kg$ (emu/g). When the saturation magnetization of the magnetic carrier is less than 20 $A \cdot m^2/kg$, the sensitivity of the magnetic carrier to the magnetic field tends to become low, degrading the collection efficiency. When the saturation magnetization of the magnetic carrier exceeds 100 $A \cdot m^2/kg$, the magnetic carriers easily cohere magnetically, and tend to show degraded dispersibility in the purification system of the protein. The saturation magnetization of the magnetic carrier can be determined by, for example, measuring the magnetization upon application of 796.5 kA/m (10 kilooersted) magnetic field using a vibrating sample magnetometer (manufactured by TOEI INDUSTRY CO., LTD).

While the magnetic carrier is magnetized to some degree by the magnetic field applied for collection, a greater coercive force causes a greater coherence between magnetic carriers, which in turn degrades dispersibility of the magnetic carrier during elution of protein from the magnetic carrier. As a result, the elution property of the bound protein in the solution is degraded and the extraction efficiency tends to become lower. The coercive force does not cause any particular problem while it is small, but a small coercive force is achieved only with the restriction on the kind of ferromagnetic iron oxide particle to be used and the synthesis method of the magnetic carrier.

The magnetic carrier of the present invention preferably has a coercive force of not more than 15.93 kA/m (200 oersted), more preferably 2.39 kA/m–11.94 kA/m (30 oersted–150 oersted). The coercive force of the magnetic carrier can be determined using a vibration sample magnetometer (manufactured by TOEI INDUSTRY CO., LTD) by, for example, applying the magnetic field of 796.5 kA/m (10 kilooersted) for saturation magnetization, reducing the magnetic-field to nil, applying the magnetic field such that the magnetic field gradually increases in the reverse direction and reading the intensity of the applied magnetic field at the time when the magnetization value becomes nil.

The magnetic carrier of the present invention preferably shows a saturation magnetization of 20 $A \cdot m^2/kg$ (emu/g) –100 $A \cdot m^2/kg$ (emu/g), and a coercive force thereof of not more than 15.93 kA·m (200 oersted), in consideration of the well-balanced collection efficiency and dispersibility of the magnetic carrier in the purification method of protein utilizing the magnetic field to be mentioned below.

In a particularly preferable embodiment, the magnetic carrier of the present invention contains a ferromagnetic oxide particle and a carbohydrate layer coating the ferromagnetic oxide particle, shows a coercive force of not more than 15.93 kA/m (200 oersted) and saturation magnetization of 20 $A \cdot m^2/kg$–100 $A \cdot m^2$ /kg and has a spherical, ellipsoidal or granular shape having an average particle size of 0.05 µm–20 µm. In this embodiment, moreover, the magnetic carrier comprises a magnetite particle as a ferromagnetic oxide particle and amylose as carbohydrate.

The protein (objective protein) to be purified using the magnetic carrier of the present invention (with which the magnetic carrier of the present invention can bind) is not particularly limited as long as it can specifically bind with a carbohydrate. The "protein" in the present specification encompasses conventionally known various carbohydrate-binding proteins, and fusion proteins (e.g., fusion protein disclosed in U.S. Pat. No. 5,643,758) having a fragment capable of specifically binding with the carbohydrate. Furthermore, fragments thereof and the like, such as peptide, oligopeptide and polypeptide, are also encompassed as long as they can specifically bind with a carbohydrate. Specific examples include carbohydrate-binding proteins such as maltose-binding protein, arabinose-binding protein, glucose-binding protein, mannose-binding protein, lectin and the like, fusion proteins containing a part or the entirety thereof and having affinity for carbohydrate [e.g., fusion protein of protein substantially free of carbohydrate bindability and a carbohydrate-binding protein (fusion protein MBP-LacZα, wherein a maltose-binding protein is bound with the amino terminal of β-galactosidase a chain to be mentioned below; fusion protein MBP-TNP1, wherein a maltose-binding protein is bound with the amino terminal of *Escherichia coli* transposase, fusion protein MBP-GFP1 wherein a maltose-binding protein is bound with the amino terminal of a green fluorescent protein, and the like)]. Of these, a maltose-binding protein, which is a malE gene product of *Escherichia coli*, is particularly preferable, because it is a periplasm protein subject to an influence of the osmotic pressure and can specifically bind with maltose and maltodextrin.

While the production method of the magnetic carrier of the present invention is free of any particular limitation, carbohydrate can be applied on the ferromagnetic oxide particle (formation of a carbohydrate layer) by, for example, adding carbohydrate to a dispersion of ferromagnetic oxide particle in a suitable dispersion medium, and heating and cooling the mixture. Such production method of the magnetic carrier of the present invention adheres carbohydrate to a ferromagnetic oxide particle utilizing the difference in solubility of carbohydrate depending on the temperature, thereby forming a carbohydrate layer.

The respective conditions for the production method of the present invention can be appropriately determined according to the ferromagnetic oxide particle and carbohydrate to be used and are not particularly limited. In the following, an embodiment using a magnetite particle as a ferromagnetic oxide particle and amylose as carbohydrate is explained in detail.

First, magnetite particles are dispersed in a dispersion medium at the ambient temperature (20° C.). The dispersion medium is free of any particular limitation, and water, ethyl alcohol, isopropyl alcohol and the like can be used. Preferred is water, which decreases the production cost. The amount of the magnetite particle to be added to the dispersion medium is free of any particular limitation, and preferably added to a concentration of 1 wt %–50 wt % to afford a uniform dispersion.

Then, amylose is added to the dispersion with stirring at the ambient temperature and the mixture is heated to about 90° C. The amount of amylose to be added to the magnetite particle is preferably 0.1 wt %–30 wt %. Because the solubility of amylose in water is generally about several % (2%–6%), the amount of water is determined to be preferably such an amount as makes the concentration of magnetite particle to be dispersed not more than this level. For example, magnetite particle (10 g) is dispersed in water (50 g) and about 0.1 g–3 g of amylose is added. After the addition of amylose, the mixture is preferably stirred at ambient temperature for about 10 min–1 hr, heated to the above-mentioned temperature and stirred for 10 min–1 hr in a heated state, whereby amylose is uniformly dispersed to allow easy formation of a uniform carbohydrate layer.

Then, the dispersion containing dissolved amylose is cooled to ambient temperature with stirring. As a result, the dissolved amylose is gradually precipitated and adheres to the surface of the magnetite particle.

In this manner, the magnetic carrier of the present invention comprising a magnetite particle and a carbohydrate layer made from amylose for coating the magnetite particle can be produced. The magnetic carrier showing the above-mentioned saturation magnetization and coercive force can be obtained by, for example, coating 1–100 ferromagnetic oxide particles per one magnetic carrier with a carbohydrate layer, and making the proportion of the carbohydrate 0.1 wt %–30 wt % relative to the ferromagnetic oxide particle, in the above-mentioned production method of the magnetic carrier.

The magnetic carrier of the present invention is not limited to the one obtained by the aforementioned production method of the present invention, and may be obtained by a production method other than the above-mentioned, as long as the same constitution is afforded.

The magnetic carrier of the present invention is superior in preservation stability, and can be preferably used for a purification method of a protein. Even when preserved in a dispersion solution at 2–10° C. (particularly 4° C.) for 30 days, a preferable magnetic carrier of the present invention maintains not less than 80% (preferably not less than 90%) of the protein binding capability before the preservation. As used herein, the "dispersion solution" is exemplified by a buffer, such as potassium phosphate buffer, sodium phosphate buffer, Tris hydrochloride buffer, PIPES buffer, borate buffer, acetate buffer, MES buffer and the like, with preference given to 20 mM–100 mM potassium phosphate buffer (pH 5.0–8.0). The "protein binding capability" here means a protein amount that can be purified with 1 g of the particle. The protein amount can be determined by the following quantitative determination method by SDS-PAGE and measurement of absorbance (280 nm).

[Quantitative Determination of Protein by SDS-PAGE]

The quantitative determination of protein by SDS-PAGE is conducted as in the following. First, dilution series (e.g., 2-fold, 4-fold, 8-fold and the like) of a standard protein (e.g., bovine serum albumin), whose concentration is known, and a target protein are each prepared, and subjected to SDS-PAGE. Then, the smallest detectable concentration (A) for SDS-PAGE is determined from the dilution series of the standard protein and the dilution fold that permits detection of the target protein is determined from the dilution series of the target protein, the protein concentration of which being taken as the above-mentioned (A), and the concentration of the target protein is determined by multiplying with the dilution fold. SDS-PAGE is conducted according to a known method such as the method described in, for example, electrophoresis experiment method (Japanese Electrophoresis Society ed., 1999 issue) and the like.

The quantitative determination by SDS-PAGE can be also conducted by measuring the absorbance at 280 nm of the protein.

The magnetic carrier of the present invention preferably has a relatively high affinity for a fusion protein containing a part or the entirety of a protein capable of specifically binding with the aforementioned carbohydrate and having affinity for carbohydrate, rather than the protein itself. As mentioned below, the magnetic carrier of the present invention having such property can be preferably used for purifying a fusion protein containing a part or the entirety of a protein capable of specifically binding with carbohydrate and having affinity for carbohydrate from a biological sample containing the fusion protein. Preferably, when a lysate of a recombinant expressed a protein capable of specifically binding with carbohydrate and having affinity for carbohydrate and a fusion protein containing a part or the entirety of the protein capable of specifically binding with carbohydrate and having affinity for carbohydrate is purified (specifically when purified according to the methods of Experimental Example 4 and Experimental Example 5), a magnetic carrier that substantially binds 100% with the fusion protein can be obtained. As used herein, "substantially binds 100% with the fusion protein" means that the amount of a protein other than a fusion protein containing a protein capable of specifically binding with carbohydrate, which binds with a magnetic carrier, is less than the detection limit. The amount of a protein which binds with a magnetic carrier can be determined by the above-mentioned quantitative determination by SDS-PAGE and measurement of absorbance (280 nm). In other words, "substantially binds 100% with the fusion protein" means that a protein other than the fusion protein binds in an amount not detectable by these protein quantitative determination methods.

Furthermore, the magnetic carrier of the present invention is preferably characterized in that more efficient elution can be achieved than by the use of a different buffer, when phosphate buffer is used as an eluent for the elution of a protein bound with a carrier. The specificity of elution to a particular kind of buffer means the presence or otherwise of elution can be controlled by the buffer to be used. A significant effect can be expected from the use of the carrier of the present invention as a carrier for immobilizing an enzyme, because the immobilized enzyme can have a longer life. Preferably, the recovery percentage of the protein bound with a carrier is not less than 60% (preferably not less than 80%) when phosphate buffer is used, whereas not more than 20% (preferably not more than 10%) when a different buffer is used. Examples of the phosphate buffer include potassium phosphate buffer, sodium phosphate buffer and the like, of which 20 mM–100 mM potassium phosphate buffer (pH 6.0–8.0) is preferable, particularly 50 mM potassium phosphate buffer (pH 7.5) is preferable. As the different buffer here, 20 mM–100 mM Tris hydrochloride buffer, Tris sulfate buffer, HEPES buffer, MOPS buffer, PIPES buffer, borate buffer and the like can be used, and particularly, 50 mM Tris hydrochloride buffer (pH 7.5), Tris sulfate buffer (pH 8.0), HEPES buffer (pH 7.7), MOPS buffer (pH 7.5), PIPES buffer (pH 7.5) and borate buffer (pH 8.0) can be used. As used herein, a protein is eluted using, for example, a buffer containing 1 mM–100 mM (preferably 10 mM) maltose when the objective protein is a maltose-binding protein. The "recovery percentage of protein" is a ratio of the amount of the protein obtained (recovered) by purification using a magnetic carrier and a purified protein as a sample to the amount of the protein in the (original) sample. The protein amount can be determined by the above-mentioned quantitative determination by SDS-PAGE and measurement of absorbance (280 nm).

The present invention also provides a method for purifying a protein capable of specifically binding with carbohydrate from a biological sample containing the protein, using the aforementioned magnetic carrier. The purification method of protein of the present invention comprises the steps of [1] binding the above-mentioned protein with the magnetic carrier, [2] isolating the protein bound with the magnetic carrier from a biological sample, and [3] separating the protein isolated from the biological sample from the magnetic carrier, whereby the protein is purified.

In step [1], a biological sample containing the objective protein and a magnetic carrier are mixed to allow the objective protein to bind with the magnetic carrier. The method for binding the objective protein with the magnetic carrier is free of any particular limitation as long as they are mixed in a suitable buffer to bring them into contact with each other. The mixing is sufficiently achieved by, for example, gently reversing the tube to allow stirring or shaking the tube, which is done using, for example, a commercially available vortex mixer and the like.

When step [1] is conducted, the magnetic carrier is preferably prepared in advance by dispersing same in a suitable dispersion medium to give a solution for protein extraction. The dispersion medium, in which the magnetic carrier has been dispersed, is free of any particular limitation, but potassium phosphate buffer, sodium phosphate buffer, Tris hydrochloride buffer, PIPES buffer, borate buffer and the like are preferable, because they are generally used for purification of proteins. Of these, 20 mM–100 mM potassium phosphate buffer (pH 6.0–8.0) is preferably used.

For preparation of a solution for protein extraction, a magnetic carrier is preferably added such that the concentration of the dispersion solution is 0.1 g/mL–1.0 g/mL. When it is less than 0.1 g/mL, retention of many proteins becomes difficult and magnetic collectivity tends to become poor, and when it exceeds 1.0 g/mL, dispersibility and preservation stability of the dispersion solution tend to become poor.

While the mixing ratio of the solution for protein extraction and the biological sample varies depending on the molecular weight of the objective protein, it preferably makes the weight ratio of the magnetic carrier:objective protein contained in the biological sample 1:0.001–1:0.1.

In the subsequent step [2], the objective protein bound with the magnetic carrier in the above-mentioned step [1] is isolated from the biological sample together with the magnetic carrier. The isolation can be done by centrifugal separation or filter separation, but a magnetic field, i.e., magnet, is preferably used for the isolation, because the operation is simple and specific isolation can be done in a short time, which in turn affords miniaturization of the purification apparatus as a whole, continuous treatment and facilitated automation treatment. The magnet to be preferably used is, for example, one having a magnetic flux density of about 0.03 T (300 gauss). Specifically, the above-mentioned step [1] is conducted in a suitable tube, and after binding of the magnetic carrier with the objective protein, a magnet is placed near the side wall of the tube to pull together the magnetic carrier bound with the objective protein near the side wall of the tube, and the remaining solution is discharged from the tube while maintaining this state.

In step [3], the objective protein isolated from the biological sample as mentioned above is separated from the magnetic carrier. In this step, for example, a solution for elution, that can elute the protein, is injected into the tube after step [2] to cause elution of the protein from the magnetic carrier. Thereafter, the magnetic carrier is collected using the magnet and removed from the tube to separate the objective protein from the magnetic carrier.

As the above-mentioned solution for elution that can elute the protein, a solution containing carbohydrate having affinity for the protein is preferably used. For example, when the objective protein is a maltose-binding protein, a buffer containing 1 mM–100 mM maltose can be exemplified. As the buffer, potassium phosphate buffer, sodium phosphate buffer, Tris hydrochloride buffer, PIPES buffer, borate buffer and the like can be mentioned, of which 20 mM–100 mM potassium phosphate buffer (pH 6.0–8.0) is preferable.

By the purification method basically containing the above-mentioned steps [1]–[3], the objective protein can be purified from a biological sample. The purification method of the present invention affords dramatically improved convenience when compared to conventional methods, and permits automation and high throughput.

Moreover, the present invention provides, using the aforementioned magnetic carrier, a method for purifying a fusion protein containing a part or the entirety of a protein capable of specifically binding with carbohydrate and having affinity for carbohydrate from a biological sample containing the protein and the fusion protein. The purification method of the fusion protein of the present invention comprises the steps of [1] binding the above-mentioned fusion protein with the magnetic carrier, [2] isolating the fusion protein bound with the magnetic carrier from a biological sample, and [3] separating the fusion protein bound with the magnetic carrier isolated from the biological sample, from the magnetic carrier, whereby the fusion protein can be purified. The respective steps [1]–[3] can be carried out according to the above-mentioned purification method of a protein capable of specifically binding with carbohydrate. By the purification method basically containing the above-mentioned steps [1]–[3], the objective fusion protein can be purified from a biological sample containing a protein capable of specifically binding with carbohydrate and a fusion protein containing said protein. The purification method of the present invention affords dramatically improved convenience when compared to conventional methods, and permits automation and high throughput.

The magnetic carrier of the present invention may be provided as a reagent kit for purification of protein, which contains a magnetic carrier, a dispersion medium for dispersing the magnetic carrier for preparation of the above-mentioned solution for protein extraction and the aforementioned solution for elution capable of eluting the protein, or the above-mentioned solution for protein extraction containing the magnetic carrier and the aforementioned solution for elution capable of eluting the protein, which are contained in separate tubes and the like. Such reagent kit of the present invention omits the labor of preparing various reagents and the like for purification of protein and makes it possible to quickly apply the method of the present invention using only the necessary amounts.

The present invention is described in more detail in the following by way of Examples, which are not to be construed as limitative.

EXAMPLE 1

<Synthesis of Magnetite Particle>

The magnetite particle to be subjected to an adhesion treatment with amylose was synthesized according to the following method. Ferrous sulfate ($FeSO_4 \cdot 7H_2O$, 100 g) was dissolved in pure water (1000 cc). Sodium hydroxide (28.8 g) was dissolved in 500 cc of pure water to achieve equimolar with the ferrous sulfate. Then aqueous solution of sodium hydroxide was added dropwise over 1 hr while stirring to an aqueous ferrous sulfate solution to precipitate ferrous hydroxide. After the completion of the dropwise addition, the suspension containing the precipitated ferrous hydroxide was heated to 85° C. with stirring. After the temperature of the suspension reached 85° C., the reaction mixture was oxidized for 8 hr while blowing in air at a rate of 200 L/hr with an air pump to give magnetite particles. The magnetite particles were almost spherical and had an average particle size of 0.28 μm.

The average particle size of the magnetite particle was determined by measuring the size of 300 particles on a transmission electron microscopic photograph and calculating a number average thereof.

<Amylose Adhesion Treatment>

The magnetite particles (10 g) synthesized as mentioned above were dispersed in 50 cc of pure water. Amylose (1 g) was added to the dispersion solution at the ambient temperature (20° C.) and the mixture was stirred for 30 min, then heated to 90° C. with stirring. After stirring at 90° C. for 1 hr, the mixture was allowed to cool to room temperature with stirring. Because amylose is easily dissolved by heating and does not dissolve easily when cooled, amylose precipitates on the surface of magnetite particle in this cooling step. In this manner, a magnetic carrier (amylose-coated magnetite particle), wherein the magnetite particle is coated with a carbohydrate layer made from amylose, was prepared.

The obtained amylose-coated magnetite particle had a spherical or granular shape and had an average particle size of 0.6 μm. It showed saturation magnetization of 75.1 $A \cdot m^2/kg$ (emu/g) and a coercive force of 7.17 kA/m (90 oersted) as measured by applying a magnetic field of 796.5 kA/m (10 kilooersted) using a vibrating sample magnetometer (manufactured by TOEI INDUSTRY CO., LTD.).

EXAMPLE 2

In the same manner as in Example 1 except that magnetite particle was synthesized after changing the temperature of the suspension containing the ferrous hydroxide precipitate from 85° C. to 60° C., a magnetic carrier (amylose-coated magnetite particle) was prepared.

The synthesized magnetite particle had a spherical shape and had an average particle size of 0.13 μm. The obtained amylose-coated magnetite particle had a spherical or granular shape and had an average particle size of 0.4 μm. It showed saturation magnetization of 73.8 $A \cdot m^2/kg$ (emu/g) and a coercive force of 8.36 kA/m (105 oersted) as measured in the same manner as in Example 1.

EXAMPLE 3

In the same manner as in Example 1 except that the amylose adhesion treatment was conducted after changing the amount of amylose added from 1 g to 2 g, a magnetic carrier (amylose-coated magnetite particle) was prepared.

The obtained amylose-coated magnetite particle had a spherical or granular shape and had an average particle size of 0.8 μm. It showed saturation magnetization of 69.7 $A \cdot m^2/kg$ (emu/g) and a coercive force of 7.57 kA/m (95 oersted) as measured in the same manner as in Example 1.

EXPERIMENTAL EXAMPLES 1–3

Using the amylose-coated magnetite particles prepared in Examples 1–3 and according to the following processes, the objective proteins were extracted and purified from biological samples.

As a biological sample for isolating the protein, bacterial cells obtained by culturing *Escherichia coli* (*Escherichia coli* JM109 (available from Toyobo co., Ltd.)) retaining plasmid pMALc2E (plasmid that expresses fusion protein MBP-LacZα wherein a maltose-binding protein is bound with the amino terminal of β-galactosidase α chain, available from New England Biolab) in 50 mL TB medium/500 mL flask at 37° C. for 20 hr were used. The bacterial cells were suspended in 50 mM potassium phosphate buffer (pH 7.5) such that the bacterial cell turbidity (OD 660 nm) was 20, and intermittently ultrasonicated for 9 min. The supernatant was separated by centrifugation and used as a biological sample for protein purification.

The above-mentioned respective amylose-coated magnetite particles were dispersed in 50 mM potassium phosphate buffer (pH 7.5) at 0.2 g/mL. The respective amylose-coated magnetite particle dispersion solution (100 μL) was mixed with a biological sample (1 mL) to give a mixed solution. After solid-liquid separation, the solid was washed with a washing solution (50 mM potassium phosphate buffer, pH 7.5). As a solution for elution to recover a protein bound with amylose-coated magnetite particle, 50 mM potassium phosphate buffer (pH 7.5) containing 10 mM maltose was used.

Specific steps were as follows.

(1) The bacterial cell turbidity (OD 660 nm) of each mixed solution was measured and the bacterial cell was separated by centrifugation using a centrifugation tube. Then the bacterial cell was suspended in 50 mM potassium phosphate buffer (pH 7.5) such that the bacterial cell turbidity was 20, and intermittently ultrasonicated for 9 min. The supernatant was separated by centrifugation.
(2) The supernatant (1 mL) was placed in a 1.5 cc eppendorf tube to give a biological sample, to which amylose-coated magnetite particle dispersion solution (100 µL) was added, which was followed by mixing for about 5 min.
(3) The above-mentioned tube was set on a magnet stand having a shape fitting the 1.5 cc eppendorf tube to collect the amylose-coated magnetite particle toward the magnet side.
(4) The solution was sucked with a filter tip and discharged.
(5) The tube was removed from the magnet stand and 1 cc of a washing solution (50 mM potassium phosphate buffer, pH 7.5) was poured therein.
(6) After thorough mixing with the amylose-coated magnetite particle, the mixture was again placed on the magnet stand and the solution was discharged in the same manner as above.

To the amylose-coated magnetite particle bound with the protein by the method mentioned above, a 50 mM potassium phosphate buffer (pH 7.5, 50 µL) containing 10 mM maltose was added, which was followed by mixing for about 5 min. The mixture was set on a magnet stand, from which a recovered solution was sucked with a filter tip, and placed in a fresh tube. The amount recovered was 40 µL. The recovered protein was measured for absorbance (OD: 280 nm) using an absorbance meter and the concentration was determined. The recovered amount of the protein was calculated by multiplying the above-mentioned protein concentration with a recovered volume.

The results are shown in Table 1.

TABLE 1

| | Average particle size (µm) of magnetic carrier | Amount of amylose added (wt %) | Saturation magnetization (A · m²/kg) | Coercive force (kA/m) | Amount of recovered protein (µg) |
|---|---|---|---|---|---|
| Experimental Example 1 | 0.6 | 10 | 75.1 | 7.17 | 72 |
| Experimental Example 2 | 0.4 | 10 | 73.8 | 8.36 | 84 |
| Experimental Example 3 | 0.8 | 20 | 69.7 | 7.57 | 123 |

Figure 1B:
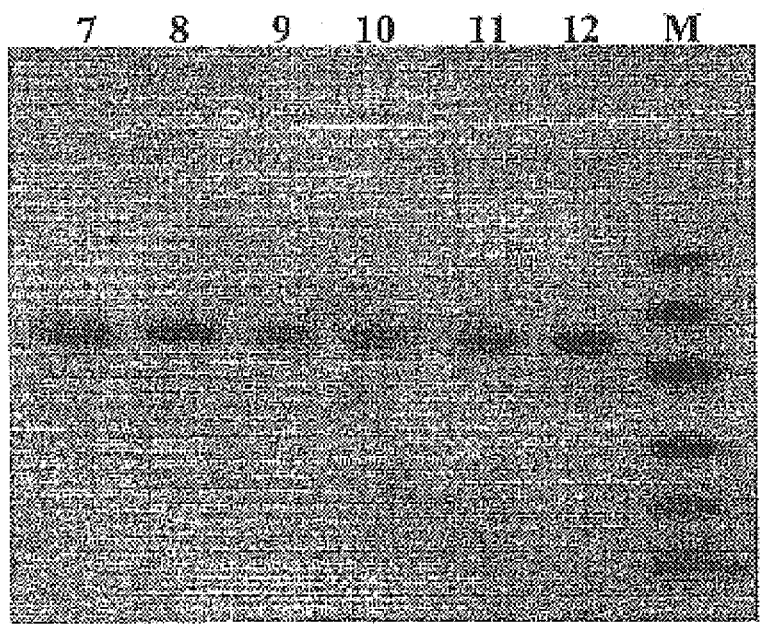
FIG. 1(b) shows comparison results achieved with purified fusion protein MBP-LacZα wherein a maltose-binding protein is bound with the amino terminal of β-galactosidase α chain purified by the present method.

FIG. 1 shows comparison of the results of SDS-PAGE of a biological sample (FIG. 1(a)), which is a mixed solution of various proteins before purification, and fusion protein MBP-LacZα (FIG. 1(b)) purified by the present method. As is clear from FIG. 1, a protein having a high purity can be obtained by extremely convenient steps according to the present method.

EXPERIMENTAL EXAMPLE 4

Using the amylose-coated magnetite particles prepared in Example 2 and according to the following processes, the objective protein was extracted and purified from a biological sample and the stability of the magnetite particle in a dispersion solution was examined.

As a biological sample from which to isolate the protein, bacterial cells obtained by culturing *Escherichia Coli* (*Escherichia coli* JM109 (available from Toyobo co., Ltd.)) retaining plasmid (pMAL-TNP1) obtained by modifying plasmid pMALc2E to express fusion protein MBP-TNP1, wherein maltose-binding protein is bound with the amino terminal of *Escherichia coli* transposase, in 50 mL TB medium/500 mL flask at 37° C. for 20 hr were used. The bacterial cells were suspended in 50 mM potassium phosphate buffer (pH 7.5) such that the bacterial cell turbidity (OD 660 nm) was 20, and intermittently ultrasonicated for 9 min. The supernatant was separated by centrifugation and used as a biological sample for protein purification.

First, the above-mentioned amylose-coated magnetite particles were dispersed in 50 mM potassium phosphate buffer (pH 7.5) at 0.2 g/mL. The fusion protein MBP-TNP1 was purified from the above-mentioned biological sample according to the methods shown in Experimental Examples 1–3 using a dispersion solution and a dispersion solution obtained by preservation of the dispersion solution for 30 days (4° C.).

Figure 2:
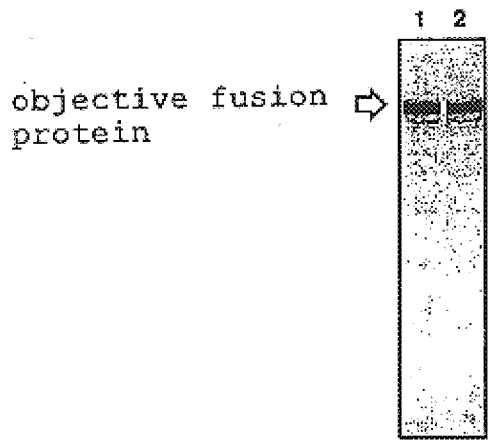
FIG. 2 shows comparison results of SDS-PAGE of respective fusion proteins MBP-TNP1 wherein a maltose-binding protein is bound with the amino terminal of *Escherichia coli* transposas purified using an amylose-coated magnetite particle immediately after dispersion and an amylose-coated magnetite particle refrigerated (4° C.) for 30 days after dispersion.

FIG. 2 shows comparison results of SDS-PAGE of each fusion protein MBP-TNP1 purified using an amylose-coated magnetite particle immediately after dispersion and an amylose-coated magnetite particle refrigerated (4° C.) for 30 days after dispersion. In addition, the protein binding capability of the amylose-coated magnetite particle immediately after dispersion and the amylose-coated magnetite particle refrigerated (4° C.) for 30 days after dispersion was determined by quantitative determination of the amount of fusion protein that can be purified using 0.2 g of amylose-coated magnetite particle by protein quantitative determination method including measurement of absorbance (280 nm). The obtained values were 500 µg/g-particle and 450 µg/g-particle. That is, it is clear that the amylose-coated magnetite particle of the present invention preserved not less than 80% of the protein binding capability before the preservation, even after refrigerated (4° C.) in the dispersion solution for 30 days.

EXPERIMENTAL EXAMPLE 5

Using the amylose-coated magnetite particles prepared in Example 2 and commercially available amylose-coated resin (available from New England Biolab), and according to the following processes, the objective protein was extracted and purified from a biological sample shown in Experimental Example 4.

The method for purifying the protein using amylose-coated magnetite particle followed Experimental Example 4. As regards the commercially available amylose-coated resin, the resin was dispersed in 50 mM potassium phosphate buffer (pH 7.5) at 0.2 g/ml. An amylose-coated resin dispersion solution (100 µL) and a biological sample (1 mL) were mixed to give a mixed solution. After solid-liquid separation, the solid was washed with a washing solution (50 mM potassium phosphate buffer, pH 7.5). As a solution for elution to recover a protein bound with amylose-coated resin, 50 mM potassium phosphate buffer (pH 7.5) containing 10 mM maltose was used.

Specific steps were as follows.

(1) The bacterial cell turbidity (OD 660 nm) of each mixed solution was measured and the bacterial cell was separated by centrifugation using a centrifugation tube. Then the bacterial cell was suspended in 50 mM potassium phosphate buffer (pH 7.5) such that the bacterial cell turbidity was 20, and intermittently ultrasonicated for 9 min. The supernatant was separated by centrifugation.

(2) The supernatant (1 mL) was placed in a 1.5 cc eppendorf tube to which amylose-coated resin dispersion solution (100 μL) was added, which was followed by mixing for about 5 min.

(3) Using an about 3 cc filtration device (available from Millipore Corporation), the mixed solution of the above-mentioned amylose-coated resin and the biological sample was filtered.

(4) To the filtration device containing the amylose-coated resin was poured 1 cc of a washing solution (50 mM potassium phosphate buffer, pH 7.5) and the mixture was thoroughly mixed and filtered.

To the amylose-coated resin bound with the protein by the above-mentioned method was added 50 mM potassium phosphate buffer (pH 7.5, 50 μL) containing 10 mM maltose and mixed for about 5 min. Using a recovery device attached to the above-mentioned filtration device, the solution was recovered.

Figure 3:
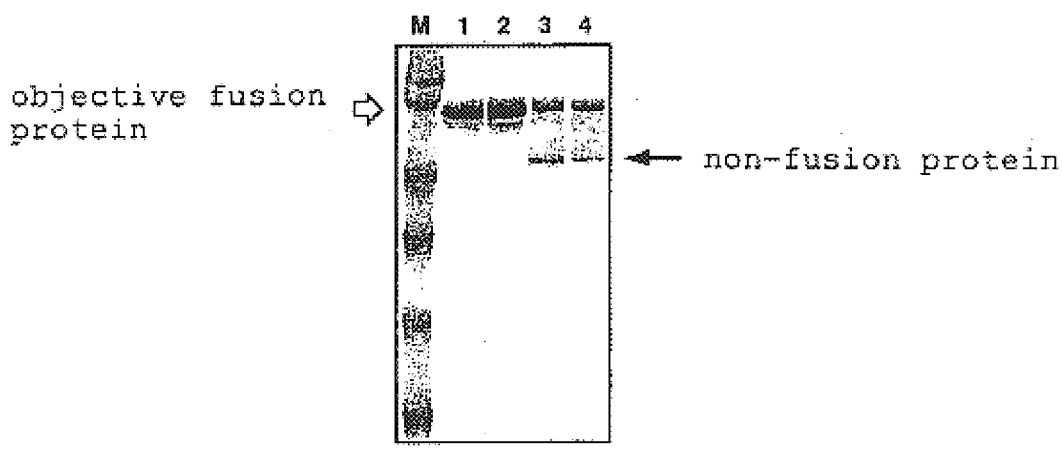
FIG. 3 shows comparison results of SDS-PAGE of respective fusion proteins MBP-TNP1 purified using an amylose-coated magnetite particle and a commercially available amylose-coated resin.

FIG. 3 shows comparison results of SDS-PAGE of each fusion protein MBP-TNP1 purified using an amylose-coated magnetite particle and a commercially available amylose-coated resin. As is clear from FIG. 3, the amylose-coated magnetite particle of the present invention has higher affinity for a fusion protein (objective fusion protein) of a protein substantially free of carbohydrate-binding property and carbohydrate-binding protein, as compared to a carbohydrate-binding protein itself (non-fusion protein).

Moreover, based on the analysis results of the amount of the purified protein and the aforementioned results of the protein quantitative determination by SDS-PAGE, the purified amount of fusion protein and non-fusion protein was measured. As a result, when a commercially available amylose-coated resin was used, a non-fusion protein on average of 0.14 μg was present per a fusion protein on average of 0.8 μg (repeat number 3). In contrast, when amylose-coated magnetite particle of the present invention was used, a non-fusion protein on average of 0 μg was present per a fusion protein on average of 4.3 μg (repeat number 3), which means that the contamination was not detected. Therefore, it was numerically established that the amylose-coated magnetite particle of the present invention has higher affinity for a fusion protein (objective fusion protein) of a protein substantially free of carbohydrate-binding property and carbohydrate-binding protein, as compared to the carbohydrate-binding protein itself (non-fusion protein).

EXPERIMENTAL EXAMPLE 6

Using the amylose-coated magnetite particles prepared in Example 2 and according to the following processes, the objective protein was extracted and purified from a biological sample shown in Experimental Example 4.

The method of purifying a protein using the amylose-coated magnetite particle followed the method of Experimental Example 4 except the composition for elution to recover the protein bound with the amylose-coated magnetite particle. In this Experimental Example, a method using 50 mM potassium phosphate buffer (pH 7.5) containing 10 mM maltose as the solution for elution and a method using 50 mM Tris hydrochloride buffer (pH 7.5) containing 10 mM maltose as the solution for elution were compared.

Figure 4:
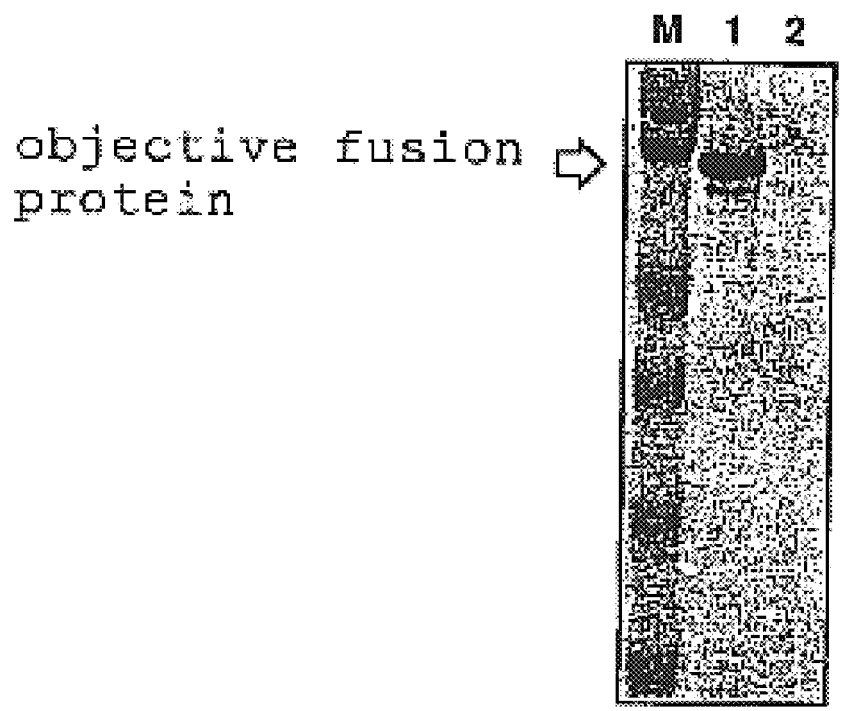
FIG. 4 shows comparison results of SDS-PAGE of respective fusion proteins MBP-TNP1 purified using 50 mM potassium phosphate buffer (pH 7.5) containing 10 mM maltose and 50 mM Tris hydrochloride buffer (pH 7.5) containing 10 mM maltose as eluents for recovering a protein bound with an amylose-coated magnetite particle.

FIG. 4 shows comparison results of SDS-PAGE of each fusion protein MBP-TNP1 purified using 50 mM potassium phosphate buffer (pH 7.5) containing 10 mM maltose and 50 mM Tris hydrochloride buffer (pH 7.5) containing 10 mM maltose as eluents for recovering a protein bound with an amylose-coated magnetite particle. As is clear from FIG. 4, the amylose-coated magnetite particle of the present invention affords more efficient elution of the protein bound with the carrier by the use of phosphate buffer than by the use of a different buffer for eluent.

The recovery percentage of protein using various elution buffers was determined by the measurement of A280 of the protein. That is, purification was carried out using a purified fusion protein as a sample, and the recovery percentage was determined from the ratio of the amount of the obtained fusion protein and that of the (original) fusion protein, which was used as the sample. As a result, the recovery percentage was as shown in the following Table 2, numerically verifying that the use of phosphate buffer as an eluent afforded more efficient elution than by the use of a different buffer.

TABLE 2

| 50 mM buffer containing 10 mM maltose | Recovery percentage (%) |
|---|---|
| potassium phosphate buffer (pH 7.5) | 80 |
| Tris hydrochloride buffer (pH 7.5) | 0 |
| Tris sulfate buffer (pH 8.0) | 0 |
| HEPES buffer (pH 7.7) | 0 |
| MOPS buffer (pH 7.5) | 0 |
| PIPES buffer (pH 7.5) | 0 |
| borate buffer (pH 8.0) | 4 |
| $H_2O$ | 0 |

According to the present invention, a convenient purification method of protein, which affords automation and high throughput, and a material therefor can be provided.

This application is based on patent application No. 2002-29751 filed in Japan, the contents of which are hereby incorporated by reference.

What is claimed is:

1. A magnetic carrier comprising a ferromagnetic oxide particle and a carbohydrate layer coating the ferromagnetic oxide particle, wherein the magnetic carrier has a saturation magnetization of 20 A·m$^2$/kg–100 A·m$^2$/kg.

2. The magnetic carrier of claim 1, wherein the ferromagnetic oxide is ferromagnetic iron oxide.

3. The magnetic carrier of claim 2, wherein the ferromagnetic iron oxide is at least one member selected from maghemite, magnetite and manganese zinc ferrite.

4. The magnetic carrier of claim 1, wherein the carbohydrate forming the carbohydrate layer is oligosaccharide or polysaccharide comprising glucose as a main unit.

5. The magnetic carrier of claim 4, wherein the carbohydrate forming the carbohydrate layer is amylose.

6. The magnetic carrier of claim 1, showing a coercive force of not more than 15.93 kA/m.

7. The magnetic carrier of claim 1, having an average particle size of 0.05 μm–20 μm.

8. The magnetic carrier of claim 1, which has relatively high affinity for a fusion protein containing a part or the entirety of a protein capable of specifically binding with carbohydrate and having affinity for carbohydrate, rather than the protein itself.

9. The magnetic carrier of claim 8, which substantially binds 100% with a fusion protein containing a part or the entirety of a protein capable of specifically binding with carbohydrate and having affinity for carbohydrate, when a lysate of a recombinant that expresses the protein and the fusion protein is purified.

10. A production method of the magnetic carrier of claim 1, which comprises adding a carbohydrate to a dispersion of the ferromagnetic oxide particles, heating the mixture and cooling the mixture to form a carbohydrate layer coating the ferromagnetic oxide particles.

11. A method for purifying a protein capable of specifically binding with carbohydrate from a biological sample containing the protein, which comprises the steps of
   (a) binding said protein with the magnetic carrier of claim 1,
   (b) isolating said protein bound with the magnetic carrier from the biological sample, and
   (c) separating said protein isolated from the biological sample from the magnetic carrier.

12. A method for purifying a fusion protein containing a part or the entirety of a protein capable of specifically binding with carbohydrate and having affinity for carbohydrate from a biological sample containing the protein and the fusion protein, which comprises the steps of
   (a) binding said fusion protein with the magnetic carrier of claim 1,
   (b) isolating said fusion protein bound with the magnetic carrier from the biological sample, and
   (c) separating said fusion protein isolated from the biological sample, from the magnetic carrier.

13. A reagent kit for purification of a protein, which comprises the magnetic carrier of claim 1, a dispersion medium for preparing a solution for protein extraction by dispersing the magnetic carrier, and an eluent capable of eluting the protein.

14. A reagent kit for purification of a protein, which comprises a solution for protein extraction containing the magnetic carrier of claim 1 and an eluent capable of eluting the protein.

15. A magnetic carrier comprising a ferromagnetic oxide particle and a carbohydrate layer coating the ferromagnetic oxide particle, which maintains, after preservation in a dispersion solution at 2–10° C. for 30 days, not less than 80% of the protein binding capability before the preservation.

16. A magnetic carrier comprising a ferromagnetic oxide particle and a carbohydrate layer coating the ferromagnetic oxide particle, which affords more efficient elution of a protein bound with said carrier by the use of a phosphate buffer as an eluent for the elution than by the use of a different buffer, wherein the protein bound with the carrier shows a recovery percentage of not less than 60% by a phosphate buffer and not more than 20% by a different buffer.

17. A magnetic carrier comprising a ferromagnetic oxide particle and a carbohydrate layer coating the ferromagnetic oxide particle, wherein a potassium phosphate buffer is used as an eluent for elution of a protein bound with a carrier.

18. The magnetic carrier of claim 1, which maintains, after preservation in a dispersion solution at 2–10° C. for 30 days, not less than 80% of the protein binding capability before the preservation.

19. The magnetic carrier of claim 1, which affords more efficient elution by the use of a phosphate buffer as an eluent for elution of a protein bound with a carrier, than by the use of a different buffer.

20. The magnetic carrier of claim 19, wherein protein bound with a carrier shows a recovery percentage of not less than 60% by a phosphate buffer and not more than 20% by a different buffer.

* * * * *